United States Patent [19]
Ono et al.

[11] Patent Number: 5,811,305
[45] Date of Patent: Sep. 22, 1998

[54] ANALYTICAL METHOD FOR EVALUATING FLAVOR STABILITY OF FERMENTED ALCOHOLIC BEVERAGES USING ELECTRON SPIN RESONANCE

[75] Inventors: Miyoko Ono; Masaaki Uchida, both of Osaka, Japan

[73] Assignee: Suntory Limited, Osaka, Japan

[21] Appl. No.: 580,201

[22] Filed: Dec. 28, 1995

[30] Foreign Application Priority Data

Dec. 28, 1994 [JP] Japan ...................................... 6-327346
Sep. 13, 1995 [JP] Japan ...................................... 7-235491

[51] Int. Cl.$^6$ .................................................. G01N 33/14
[52] U.S. Cl. .............................. 436/24; 436/173; 426/11; 426/231; 426/534; 426/592; 426/650; 324/316; 324/314
[58] Field of Search ........................ 436/24, 173; 426/11, 426/534, 592, 650, 231; 324/316, 317

[56] References Cited

FOREIGN PATENT DOCUMENTS 4168362  6/1992  Japan.
44169197 6/1992  Japan.

OTHER PUBLICATIONS

Osawa, Y. et al "ESR Studies on the Variability of Wines During Their Evolution"; Conference Proceedings, 1990, 496–500 (Abstract Only).
Gemperle C. et al. "Identification of Irradiated Berrie"; Mitteilungen aus dem Gebiete der Leben smitteluntersuchung und Hygiene; 1994, 85, 6, 751–758.
J.D. Mayhoffer, "The Automatic Measurement of Oxygen in Package Beer", *Advances in Instrumentation,* vol. 35, 1980, USA, pp. 141–148.
R.W. Kitchen et al., "Detection of Methanol in Wine by Microwave Spectroscopy", *Analytical Chemistry,* vol. 53, 1981, USA, pp. 1190–1192.

(List continued on next page.)

*Primary Examiner*—Jill Warden
*Assistant Examiner*—Sharidan Carrillo
*Attorney, Agent, or Firm*—Burns, Doane, Swecker & Mathis, L.L.P.

[57] ABSTRACT

Quantitative determination and evaluation of the flavor stability of fermented alcoholic beverages are performed by measuring the changes of the amount of spin adduct from the formation behavior of active oxygen with passage of time using an ESR apparatus and either determining the value on the time axis of the inflection point of changes of the amounts of spin adduct (defined as the active oxygen formation lag time) or determining the amount of spin adduct after a predetermined time has elapsed after the start of measurement (defined as the active oxygen formation activity). The longer the active oxygen formation lag time or the lower the active oxygen formation activity, the greater the oxygen resistance of the fermented alcoholic beverage, thus making it possible to evaluate that fermented alcoholic beverage as having good flavor stability. In addition, if the formation behavior of active oxygen of semi-finished products in the production process is measured in the same manner, the quality of flavor stability when that semi-finished product has become a finished product can be predicted and evaluated.

18 Claims, 9 Drawing Sheets

OTHER PUBLICATIONS

Bamforth et al., "New Procedures to Improve the Flavor Stability of Beer", *J Am Soc Brew Chem,* 43(4):197–202 (1985).

Bamforth et al, "Oxygen and Oxygen Radicals in Malting and Brewing: a Review", *J Am Soc Brew Chem,* 51(3):79–88 (1983).

Clarkson et al, "Oxygen Scavenging Enzymes in Barley and Malt and Their Effects During Mashing", *J. Inst. Brew.,* 98(2):111–115 (1992).

Drost et al, "Flavor Stability", *ASBC Journal,* 48(4):124–131 (1990).

Kaneda et al, "Detection of Free Radicals in Beer Oxidation", *Journal of Food Science,* 53(3):885–888 (1988).

Kaneda et al, "The Role of Free Radicals in Beer Oxidation", *J Am Soc Brew Chem,* 47(2):49–53 (1989).

Kaneda et al, "Role of Free Radicals in Chemiluminescence Generation During the Beer Oxidation Process", *Agric. Biol. Chem.,* 54(8):2165–2166 (1990).

Kaneda et al, "Effect of Free Radicals on Haze Formation in Beer", *Journal of Agricultural and Food Chemistry,* 38(10): 1909–1912 (1990).

Kaneda et al, "Free Radical Reactions in Beer During Pasteurization", *International Journal of Food Science & Technology,* 29(2):195–200 (1994).

Parsons et al, "The Assessment and Prediction of Beer Flavour Stability", *EBC Congress,* Lecture No. 30:279–286 (1983).

ANALYTICAL METHOD FOR EVALUATING FLAVOR STABILITY OF FERMENTED ALCOHOLIC BEVERAGES USING ELECTRON SPIN RESONANCE

BACKGROUND OF INVENTION

1. Field of Invention

The present invention relates to an analytical method for evaluating the flavor stability of alcoholic beverages on the shelf, and particularly beer. More particularly, the present invention relates to a predicting method that enables the flavor stability of alcoholic beverages on the shelf to be accurately evaluated in a short time using electron spin resonance.

2. Related Art

All fermented alcoholic beverages are known to deteriorate during storage after production due to oxidation caused by oxygen contained in the finished products. For example, wine is produced while paying close attention to oxidation by being completely filled into barrels and tanks in the aging process during production, and replacing the headspace in the barrels and tanks with nitrogen gas or carbon dioxide. In addition, the addition of sulfurous acid, which also serves as an antioxidant, has employed since long ago. In the case of sake, it is well known that oxygen is involved in discoloration caused by sunlight, the most serious problem relating to deterioration.

In addition, in the case of beer, oxidation gradually progresses during storage even when only a small amount of oxygen is present. This results in reduced flavor and quality, such as the production of an extremely foul odor and taste. Although there are many aspects of this deterioration caused by oxidation that remain unclear, it is known that in beer that has been stored for a long time and in which the deterioration of flavor can be detected by human sensory analysis, various aldehydes accumulate, above a sensory threshold level, in that beer. However, it is not certain which of the aldehydes is the cause of the odor associated with beer deterioration.

For example, in the case of beer, previously proposed methods for evaluating flavor stability all involve estimating the flavor stability by evaluating the degree of oxidative deterioration of the beer. After forcibly promoting oxidative deterioration by storing finished beer at high temperatures, the degree of oxidative deterioration is evaluated using either a human sensory analysis or by measuring the total amount of increases in various aldehydes. Alternatively, another example of a method for evaluating flavor stability has been proposed wherein the reducing power of beer is measured using an oxidation-reduction indicator and so forth.

All of these processes are performed on finished beer.

In addition, deterioration of flavor and quality, such as the production of foul odor and taste, is a serious problem for brewers, and the steady production of beer for which flavor stability remains favorable for a long time is an important topic. Thus, a process that enables flavor stability to be evaluated quickly and accurately as early in the production process as possible is strongly required.

However, in addition to the former methods of the prior art requiring a long time, extending over as much as several weeks, to perform evaluation, in the case of a sensory analysis, even if a relative evaluation can be performed, it is difficult to distinguish the degree of deterioration, and it is difficult to perform an absolute evaluation or quantitative measurement. In addition, sensory analysis can only be performed by specific persons who are extremely highly trained. In the case of measurement of the total amount of increases in various aldehydes, since some of the aldehydes that are measured conversely decompose if oxidation continues to progress thereby causing their amounts to reduce, and certain specific aldehydes cannot be distinguished from indicators of oxidation, this type of measurement has been inadequate for the evaluation of flavor stability.

In addition, in the case of the latter methods as well, since the reducing power possessed by beer does not effectively function to retard the oxidative deterioration in beer, it does not always correlate with flavor stability, thus making it inadequate for evaluation of flavor stability. Thus, it was extremely difficult to predict and evaluate the flavor stability of beer on the shelf by either of these methods, and there were also problems with prediction accuracy.

Moreover, although it is extremely advantageous for brewers to be able to predict and evaluate the flavor stability of the finished beer by measuring its semi-finished product at as early a stage as possible in the production process, the processes of the prior art all were applied to the finished beer, and there has previously been no process that allows a preliminary evaluation of flavor stability of finished beer beforehand in the production process.

In the case of other fermented alcoholic beverages as well, there has been no method that allows a preliminary evaluation of flavor stability, and especially no method that allows a preliminary evaluation of flavor stability at the stage of the finished product by measuring a semi-finished product in the production process.

In order to solve the problems of the prior art described above, a first object of the present invention is to provide an analytical method for evaluating the flavor stability of fermented alcoholic beverages using electron spin resonance (ESR) that enables preliminary evaluation of flavor stability to be performed both accurately and in a short time.

In addition, a second object of the present invention is to provide an analytical method for evaluating the flavor stability of fermented alcoholic beverages using an ESR apparatus that enables preliminary evaluation of flavor stability to be performed on semi-finished fermented alcoholic beverages in the production process both accurately and in a short time.

SUMMARY OF INVENTION

In order to achieve the above-mentioned first object, the first present invention is characterized in that active oxygen, formed when fermented alcoholic beverage is placed in the presence of oxygen, is captured with a spin trapping agent, and the amount of spin adduct formed is measured using an ESR apparatus.

Moreover, the second present invention is characterized in that active oxygen, formed when a semi-finished product in the production process of a fermented alcoholic beverage is placed in the presence of oxygen, is captured with a spin trapping agent, and the amount of spin adduct formed is measured using an ESR apparatus.

DETAILED DESCRIPTION

As a result of the inventors of the present invention investigating the formation behavior of active oxygen, considered to function as an initiator of oxidative deterioration in beer, it was found that the flavor stability of the beer could be preliminarily evaluated by evaluating the oxidation resistance of that beer.

Although active oxygen is formed after a definite amount of time when beer is placed in the presence of oxygen, due to the short life of the active oxygen that is formed, it is difficult to measure its amount in that form. However, by adding a spin trapping agent to trap the active oxygen, the amount of spin adduct formed can be measured using an ESR apparatus.

Although the spin trapping agent used can be suitably selected from those which are typically commercially available according to measurement conditions, in the case of heating to a certain extent, it is preferable to use one that forms a spin adduct that is relatively stable with respect to heat such as PBN ($\alpha$-phenyl-N-t-butyl nitrone). In addition, the amount of spin adduct can be quantitatively determined by using a stable radical such as 4-Oxo-Tempo as a standard.

Quantitative determination and evaluation of the oxidation resistance, or flavor stability, of beer is performed by determining the duration of the induction period until active oxygen is formed in significant amounts, namely the value on the time axis of the inflection point by successive measuring the amount of spin adduct formed by the use of an ESR apparatus (defined as the active oxygen formation lag time), in great detail, the changes of the amounts of spin adduct formed are measured successively at a definite time and are recorded after each measurement to determine the inflection point after straight formation line is obtained, and an evaluation is performed based on the value on the time axis of said inflection point. The longer the active oxygen formation lag time, the greater the oxygen resistance of the beer, thus making it possible to evaluate whether or not the beer has good flavor stability.

Alternatively, the determination and evaluation can be performed by determining the amount of spin adduct after a predetermined time has elapsed after the start of measurement (defined as active oxygen formation activity). The lower the level of active oxygen formation activity of the beer, the greater the oxidation resistance of that beer, thus making it possible to evaluate whether or not the beer has good flavor stability. The predetermined amount of time after the start of measurement can be suitably selected according to the sample measured.

Moreover, oxidation resistance can also be evaluated for semi-finished products using a similar process on semi-finished products in a beer production process, and this can be used at that time to predict the quality of flavor stability when that semi-finished product has become a finished product. The semi-finished product referred to here can be a semi-finished product at any stage of production provided it has at least completed the wort boiling process (wort, unrefined beer, etc.).

In addition, although this predicting method was initially invented as a method to be applied to beer, it was also found that this predicting method for flavor stability can also be similarly applied to other fermented alcoholic beverages provided there is no distillation process in the production process. For example, this analytical method can be effectively used on wines, such as fruit wines, and sake. In addition, evaluation can also be performed on semi-finished products in the production process of these fermented alcoholic beverages other than beer. In the case of wine, a semi-finished product refers to semi-finished products following the must used in the fermentation process (after treatment of fruit juice), and in the case of sake, a semi-finished product refers to semi-finished products following the sake-mashing-fermentation process.

EXAMPLES

EXAMPLE 1

Finished bottled beer was opened and measured with an ESR apparatus.

Measurement using the ESR apparatus consisted of degassing the beer by centrifugation immediately after removing the cap, placing 5 g as a sample in a 14.5 ml, brown, stoppered test tube, adding 0.1 ml of 2.55M PBN, storing sealed while heating at 60° C., removing samples 10, 20, 40, 60, 80, 100, 130, 160 and 200 minutes later, and inserting each sample into the cavity resonator of the ESR apparatus. The active oxygen formed in the sample was trapped by the PBN, and the amount of spin adduct was quantitatively determined using the ESR apparatus by comparing the intensity of a standard of known concentration.

Measurement was performed using the JES-RE2X electron spin resonance system made by Nippon Denshi Co., Ltd. under the following conditions:

Magnetic field: 3350±100 Gauss

Field modulation: 100 kHz, 1 Gauss

Microwave output: 5 mW

Amplification factor: $2 \times 10^3$

Response time: 1 second

Sweep time: 8 minutes

Measuring temperature: Room temperature

Figure 1:
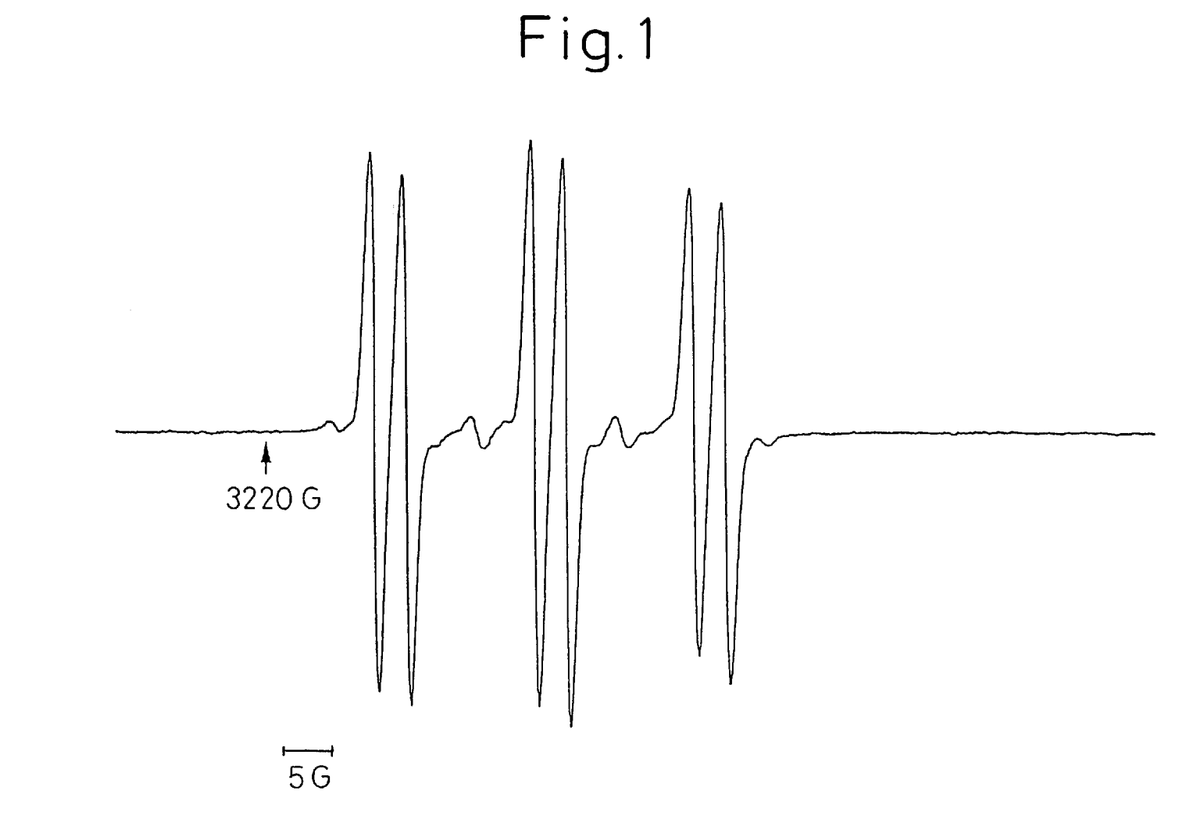
FIG. 1 is a diagram showing the ESR spectrum of hydroxyl radical in the case of using PBN as the trapping agent.

FIG. 1 shows the ESR spectrum obtained in the case of using PBN as the trapping agent. It was possible to confirm from this spectrum that the active oxygen formed in this case is a hydroxyl radical.

Figure 2:
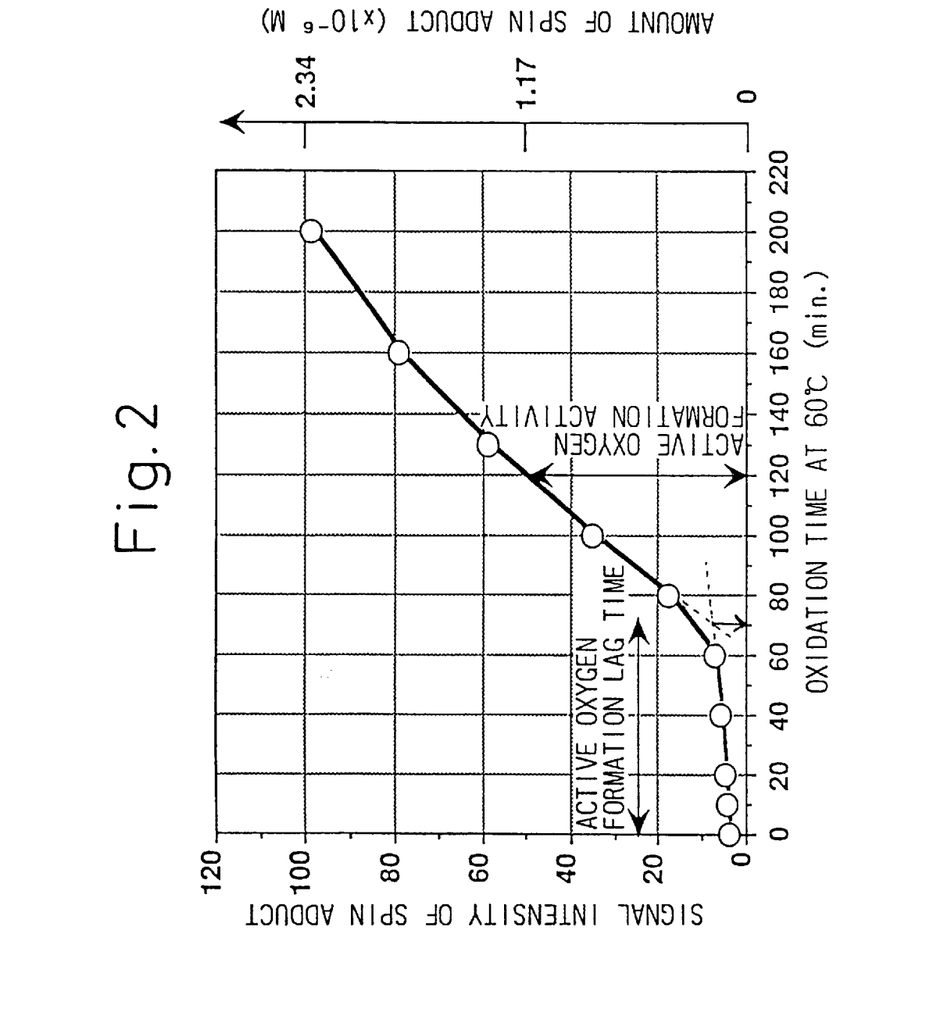
FIG. 2 is a graph expressing oxidation time at 60° C. on the horizontal axis and the magnitude of spin adduct formed on the vertical axis (example of the active oxygen formation behavior of finished beer).

FIG. 2 shows the changes of the amounts of spin adduct obtained with passage of time. When the inflection point of the changes of the amounts of spin adduct in the oxidation reaction at 60° C. of this beer is determined from this graph, it can be seen that hydroxyl radical begins to be significantly produced after 70 minutes from the start of measurement. Thus, the active oxygen formation lag time is 70 minutes and the active oxygen formation activity (spin adduct signal intensity in the case of taking the predetermined time after the start of measurement to be 120 minutes) is 50.

EXAMPLE 2

The required number of bottles of four types of finished bottled beers from different lots were obtained, one bottle of each of the four types of bottled beer was opened and measured with an ESR apparatus. The remaining bottled beer was stored unopened at 20° C., and flavor stability was continuously evaluated using a sensory analysis.

Measurement using the ESR apparatus was performed under the same conditions and following the same procedure as in Example 1. Respective graphs were obtained of changes of the amount of spin adduct with passage of time as that shown in FIG. 2. Values were then obtained for active oxygen formation lag time and active oxygen formation activity (spin adduct signal intensity in the case of taking the predetermined time after the start of measurement to be 120 minutes).

The sensory analysis was performed by storing the remaining four types of bottled beer (unopened) under identical conditions at 20° C. and opening one bottle of each every 4 weeks. The sensory analysis were performed by specially trained panelists. The panelists evaluated whether or not the degree of oxidative deterioration had reached that of a standard sample having a predetermined degree of oxidative deterioration to determine the number of weeks at which that degree of oxidative deterioration was reached.

Figure 3:
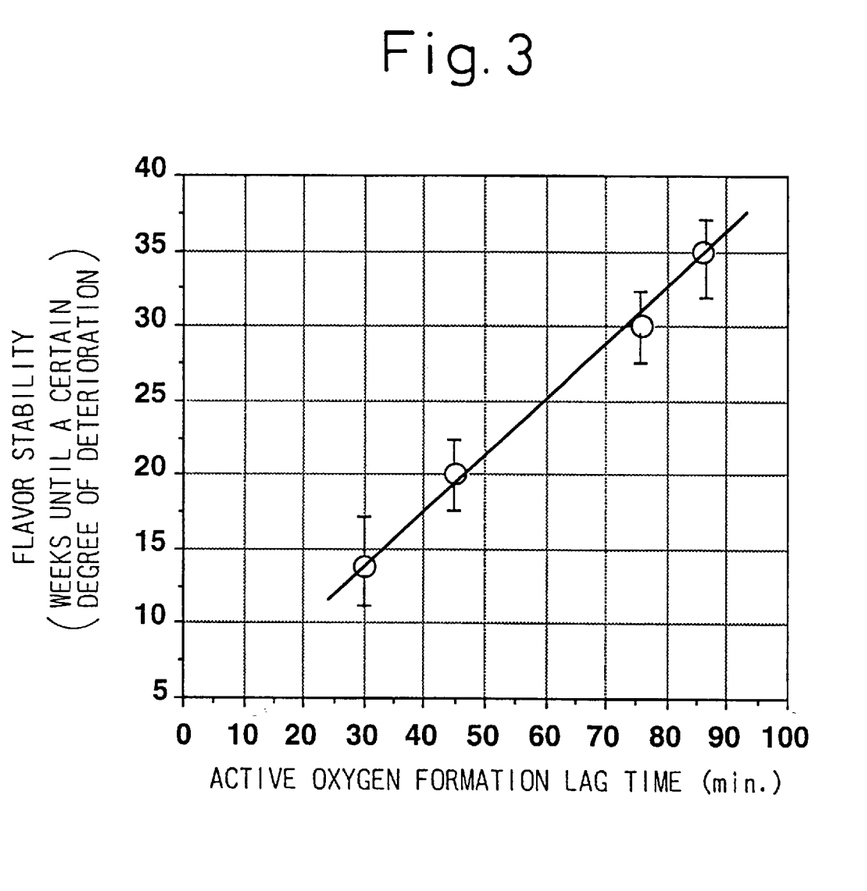
FIG. 3 is a graph expressing active oxygen formation lag time on the horizontal axis and evaluation of flavor stability obtained as a result of sensory analysis on the vertical axis for samples of four types of finished beer having different lot numbers.
Figure 4:
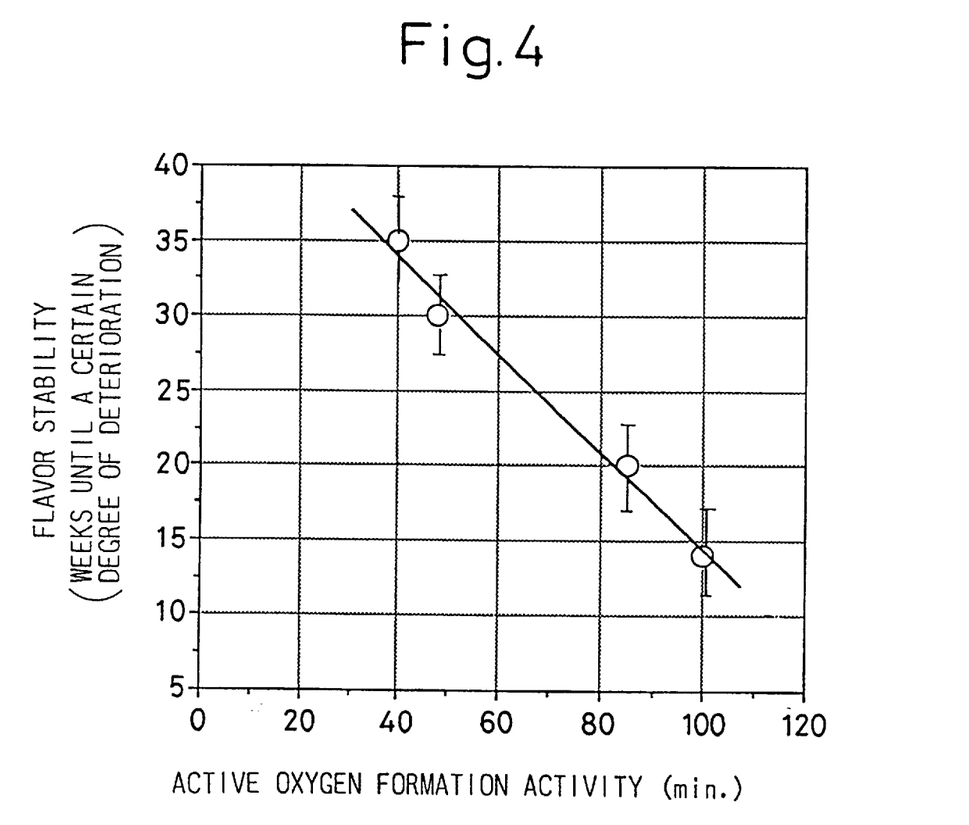
FIG. 4 is a graph expressing active oxygen formation activity on the horizontal axis and evaluation of flavor stability obtained as a result of sensory analysis on the vertical axis for samples of four types of finished beer having different lot numbers.

FIGS. 3 and 4 show the relationship between flavor stability as determined by the sensory analysis described above and the results for active oxygen formation lag time and active oxygen formation activity as determined by ESR measurement for four types of bottled beer samples having different lot numbers.

According to the results, a good correlation is observed between active oxygen formation lag time or active oxygen formation activity and flavor stability, thus indicating that it is possible to predict the flavor stability of beer according to active oxygen formation lag time or active oxygen formation activity. In addition, although flavor stability can be predicted with active oxygen formation activity as described above, in the case of finished beer, a better correlation is generally obtained between active oxygen formation lag time and flavor stability.

EXAMPLE 3

Measurements were performed on unrefined beer following completion of the fermentation process as one example of a semi-finished product in the beer production process. The two types of unrefined beer, Beer A and Beer B, different in the production process through fermentation were used. After centrifuging the unrefined beer, the resulting unrefined beer was filtered using filter paper prior to measurement. Measurements were performed under the same conditions and following the same procedure as Example 1. Namely, the measurements consisted of placing 5 g samples of the filtered unrefined beer in 14.5 ml, brown, stoppered test tubes, adding 0.1 ml of 2.55M PBN, storing sealed while heating at 60° C., removing samples at suitable intervals such as every 20 minutes, and inserting each sample into the cavity resonator of the ESR apparatus.

Evaluation of flavor stability was performed by producing beer from unrefined beers A and B by going through similar storage and filtration processes, and performing the sensory analysis described in Embodiment 2 on each of the finished beers.

Table 1 shows a comparison chart between active oxygen formation lag time of the two types of unrefined beers A and B having different production methods through fermentation, and the results of flavor stability evaluation of the finished beers produced from each of those unrefined beers A and B by going through similar storage and filtration processes.

TABLE 1

Comparison chart between active oxygen formation lag time of two types of unrefined beers A and B having different production methods through fermentation, and the results of flavor stability evaluation of the finished beers produced from each of those unrefined beers A and B by going through similar storage and filtration processes

| Unrefined Beer | Active Oxygen Formation Lag Time (min) | Finished Beer Flavor Stability (weeks) |
| --- | --- | --- |
| A | 40 | 15 |
| B | 70 | 27 |

According to those results, when the active oxygen formation lag time is long at the stage of the semi-finished product in the form of the unrefined beer, the resulting finished beer exhibited better flavor stability in comparison with a beer having a short active oxygen formation lag time. Thus, the quality of flavor stability of the finished beer can be evaluated and determined at the stage of the unrefined beer by measuring active oxygen formation lag time.

Furthermore, it was also confirmed that unrefined beer having a small value for active oxygen formation activity exhibited better flavor stability for the finished beer in comparison with unrefined beer having a large value for active oxygen formation activity.

EXAMPLE 4

Measurements were also performed on wort prior to addition of yeast and fermentation as another example of a semi-finished product in the beer production process. Measurements were performed under the same conditions and following the same procedure as Example 1 using two worts C and D having different preparation methods. Similar to the procedure of Example 1, the measurements consisted of placing 5 g samples of the wort in 14.5 ml, brown, stoppered test tubes, adding 0.1 ml of 2.55M PBN, storing sealed while heating at 60° C., removing samples at suitable intervals such as every 20 minutes, and measuring the amount of active oxygen formed using an electron spin resonance apparatus.

Figure 5:
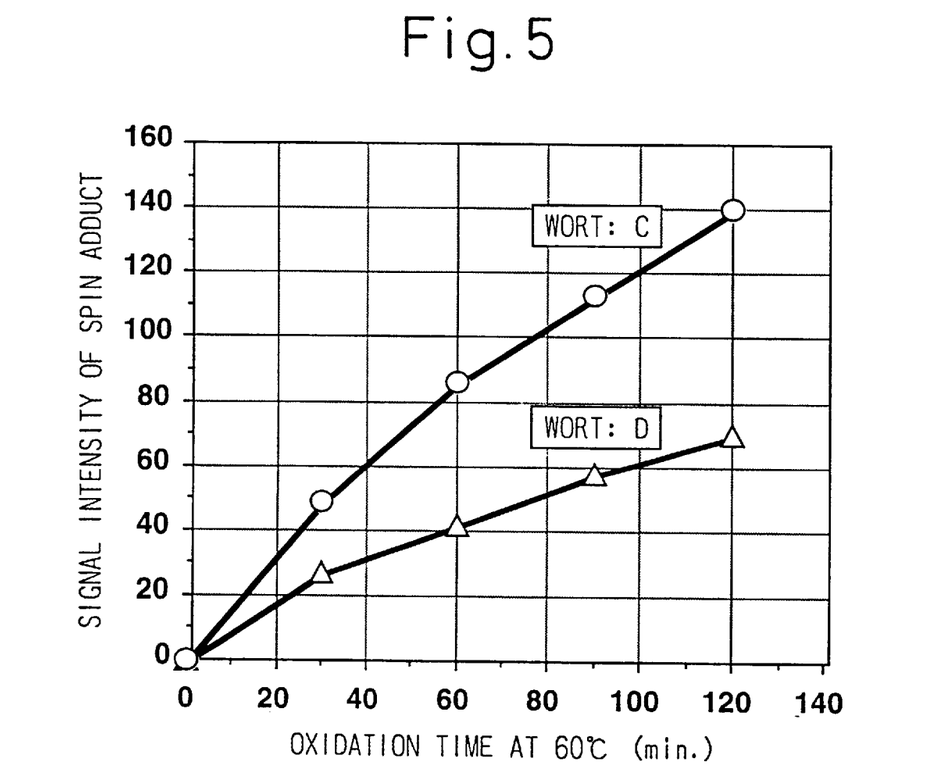
FIG. 5 is a graph expressing oxidation time at 60° C. on the horizontal axis and the magnitude of spin adduct formed on the vertical axis (example of the active oxygen formation behavior of wort).

Beer was manufactured by going through the same fermentation, storage and filtration processes using the two above worts C and D and flavor stability was evaluated by the sensory analysis described in Example 2 for each of the finished beers. FIG. 5 shows the active oxygen formation behavior of the two types of wort C and D having different preparation methods (changes of the amounts of spin adduct during oxidation reaction at. 60° C.). Table 2 is a comparison chart between the active oxygen formation activities of worts C and D (spin adduct signal intensity in the case of taking the predetermined time after the start of measurement to be 120 minutes) and the results of evaluation of flavor stability of the beers manufactured using both worts by going through the same fermentation, storage and filtration processes.

TABLE 2

Comparison chart between the active oxygen formation activities of two types of wort C and D having different preparation methods and the results of evaluation of flavor stability of the finished beers manufactured using both worts by going through the same fermentation, storage and filtration processes

| Wort | Active Oxygen Formation Activity (Spin Adduct Signal Intensity) | Finished Beer Flavor Stability (weeks) |
| --- | --- | --- |
| C | 140 | 23 |
| D | 70 | 33 |

According to those results, when the active oxygen formation activity is high at the stage of the semi-finished product in the form of the wort, the resulting finished beer was determined to have poorer flavor stability when evaluated for the finished beer in comparison with a beer having a low active oxygen formation activity. It was therefore confirmed that the quality of flavor stability of the finished beer can be evaluated at the stage of the semi-finished product in the form of the wort by measuring active oxygen formation activity.

As has been described above, it was found that the method of the present invention can be applied to both finished beer or unrefined beer and wort at the stage of the semi-finished product. In addition, according to the results obtained from this evaluation process, it was found that the flavor stability of finished beer can be effectively predicted and evaluated.

EXAMPLE 5

Figure 6:
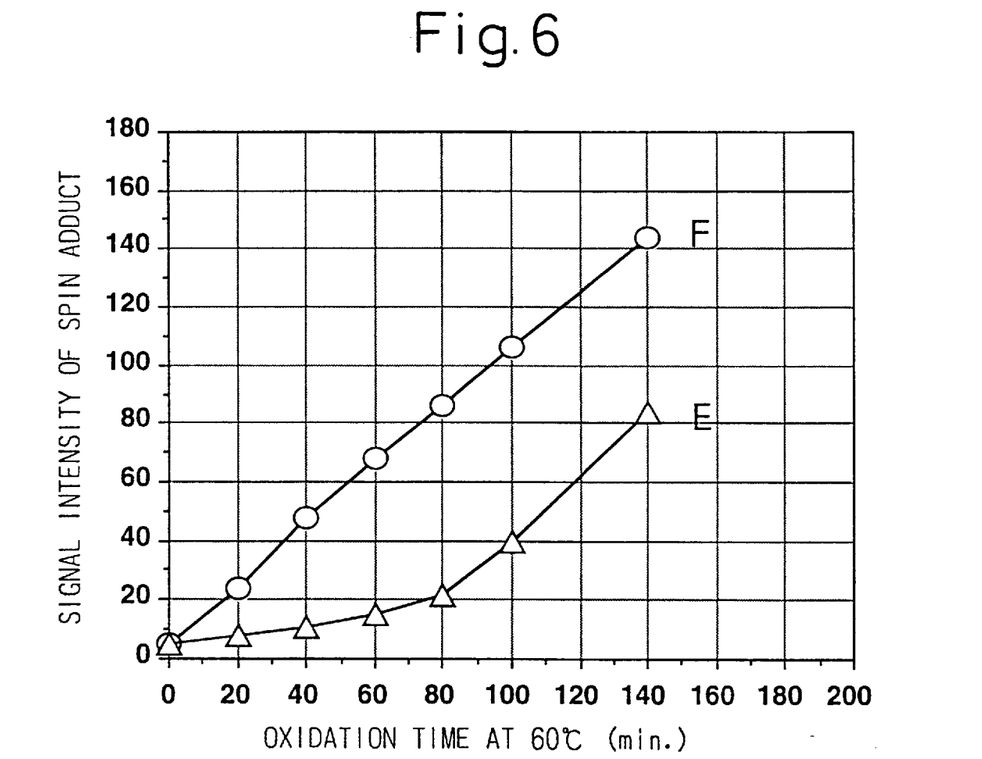
FIG. 6 is a graph expressing oxidation time at 60° C. on the horizontal axis and the magnitude of spin adduct formed on the vertical axis (example of the active oxygen formation behavior of wine).

Measurements were performed under the same conditions and following the same procedure as Example 1 using two different types of commercially available finished bottled wines E and F. In the same manner as Example 1, measurement consisted of placing 5 g samples of each wine in 14.5 ml, brown, stoppered test tubes, adding 0.1 ml of 2.55M PBN, storing sealed while heating at 60° C., removing samples at suitable intervals such as every 20 minutes, and measuring the amount of active oxygen formed using an electron spin resonance apparatus. The graphs shown in FIG. 6 were respectively obtained for changes of the amount of spin adduct with passage of time, and values were obtained for active oxygen formation lag time and active oxygen formation activity (spin adduct signal intensity in the case of taking the predetermined time after the start of measurement to be 140 minutes).

After taking out samples from the bottles of two types of finished wines E and F, immediately resealing the bottles and storing for 8 weeks at 35° C., sensory analysis were performed by four specially trained panelists on each sample. The degree of deterioration was evaluated by scoring each sample using a five point ranking system (scoring 1 for fresh and 5 for strong deterioration) and then taking the mean value of the scores given by the four panelists. Table 3 is a comparison chart between active oxygen formation activity as determined by ESR measurement of two different types of wines, and flavor stability evaluation as determined by performing sensory analysis.

TABLE 3

Comparison chart between active oxygen formation activity of two different types of finished wines E and F, and the results of evaluating flavor stability for both wines after storing for 8 weeks at 35° C.

| Wine | Active Oxygen Formation Activity (Spin Adduct Signal Intensity after 140 Minutes) | Degree of Deterioration |
| --- | --- | --- |
| E | 84 | 2.0 |
| F | 144 | 4.0 |

The degree of deterioration was evaluated using a five point ranking system assigning a score of 1 (fresh) through 5 (strong deterioration).

As compared with wine F, wine E had a longer active oxygen formation lag time and lower active oxygen formation activity. According to the results of evaluation of flavor stability using a sensory analysis after storage for 8 weeks as well, the flavor stability of wine E was confirmed to be better than wine F as a result of having a lower degree of flavor deterioration. According to those results, it was found that flavor stability can be rapidly and effectively predicted and evaluated for wines as well by determining active oxygen formation lag time or active oxygen formation activity.

EXAMPLE 6

Figure 7:
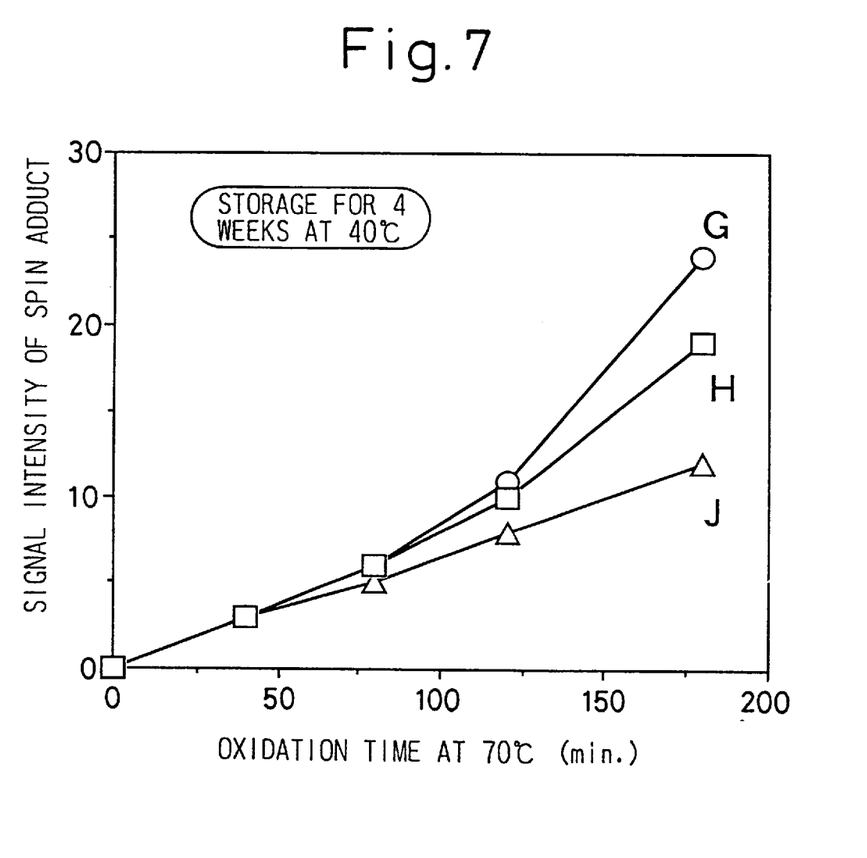
FIG. 7 is a graph expressing oxidation time at 70° C. on the horizontal axis following storage for 4 weeks at 40° C., and the magnitude of spin adduct formed on the vertical axis (example of the active oxygen formation behavior of sake).

Three different types of commercially available finished bottled sake having nearly the same production methods were stored for 4 weeks at 40° C. without opening the bottles. Measurement was performed under the same conditions and following the same procedure as Example 1 with the exception of heating at 70° C. Similar to Example 1, the measurements consisted of placing 5 g samples of each sake in 14.5 ml, brown, stoppered test tubes, adding 0.1 ml of 2.55M PBN, storing sealed while heating at 70° C., and measuring the amount of active oxygen formed using an electron spin resonance apparatus. The graphs shown in FIG. 7 were respectively obtained for changes of the amount of spin adduct with passage of time, and values were obtained for active oxygen formation lag time and active oxygen formation activity (spin adduct signal intensity in the case of taking the predetermined time after the start of measurement to be 180 minutes).

After taking out samples, following storage for 4 weeks at 40° C., from unopened bottles of three types of finished sake G, H and J, sensory analysis were performed on the remainder in each bottle by four specially trained panelists. The degree of deterioration was evaluated by scoring each sample using a five point ranking system (scoring 1 for fresh and 5 for strong deterioration) and then taking the mean value of the scores given by the four panelists. Table 4 is a comparison chart between active oxygen formation activity as determined by ESR measurement of the three different types of sake, and flavor stability evaluation as determined by performing sensory analysis.

TABLE 4

Comparison chart between active oxygen formation activity measured after storing three different type of finished sake G, H and J for 4 weeks at 40° C., and the results of evaluating flavor stability

| Sake | Active Oxygen Formation Activity (Spin Adduct Signal Intensity after 180 Minutes) | Degree of Deterioration |
| --- | --- | --- |
| G | 24 | 4.0 |
| H | 19 | 2.5 |
| J | 12 | 1.5 |

The degree of deterioration was evaluated using a five point ranking system assigning a score of 1 (fresh) through 5 (strong deterioration).

Results were obtained in which the magnitude of active oxygen formation activity for sake G, H and J was in the order of G>H>J, thus indicating differences between the three types of sake. In addition, the results of the sensory analysis yielded an order of flavor deterioration of G>H>J (in order of strongest deterioration). Thus, it was confirmed that the sake having the lowest active oxygen formation activity also had the lowest degree of flavor deterioration after storage and correspondingly the best flavor stability.

Figure 9:
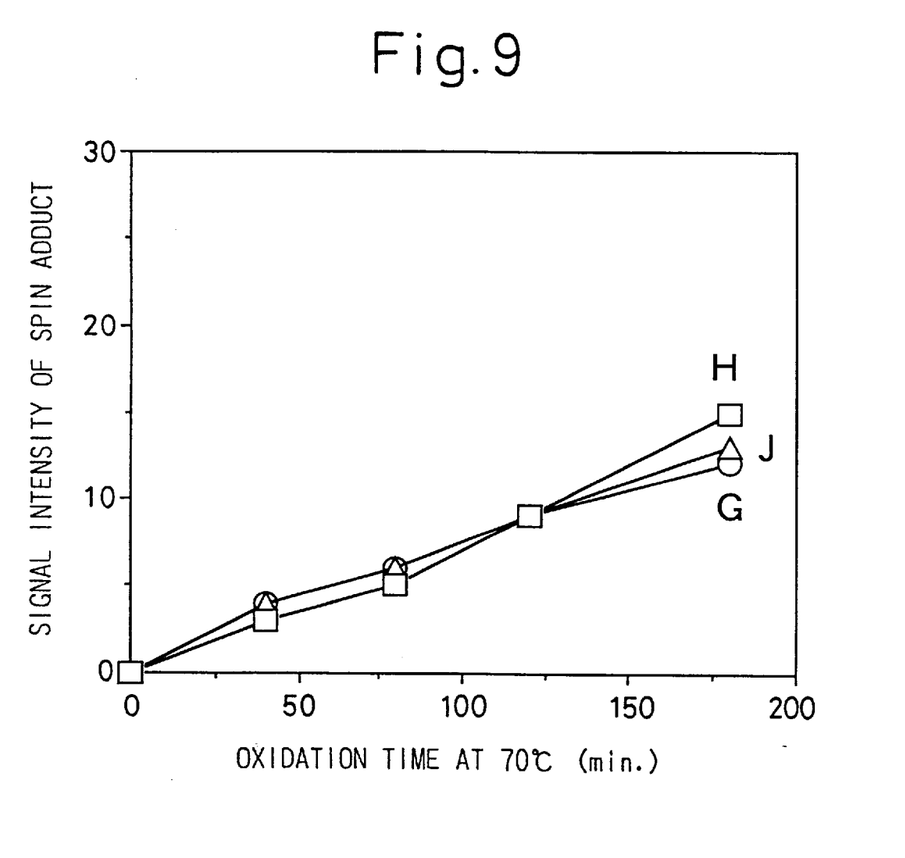
FIG. 9 is a graph expressing oxidation time at 70° C. on the horizontal axis and the magnitude of spin adduct formed on the vertical axis (example of the active oxygen formation behavior of sake).

When the active oxygen formed was measured by an electron spin resonance apparatus under the same conditions and following the same procedure as Example 6 immediately after opening the bottles of sake G, H and J used in Example 6 without storing for 4 weeks, the graphs of changes of the amount of spin adduct were respectively obtained as shown in FIG. 9. However, according to these graphs, there were no differences observed between the three types of sake with respect to active oxygen formation lag time and active oxygen formation activity. Therefore, in order to detect differences in active oxygen formation behavior between each type of sake, measurements were performed in Example 6 after storing for 4 weeks at 40° C. However, this does not allow a rapid prediction of flavor stability at the time of shipment from the factory. In order to enable measurement to be performed rapidly without storing for 4 weeks, measurement was performed under conditions of forcibly promoted oxidation by adding a constant amount of hydrogen peroxide to the sake.

EXAMPLE 7

Figure 8:
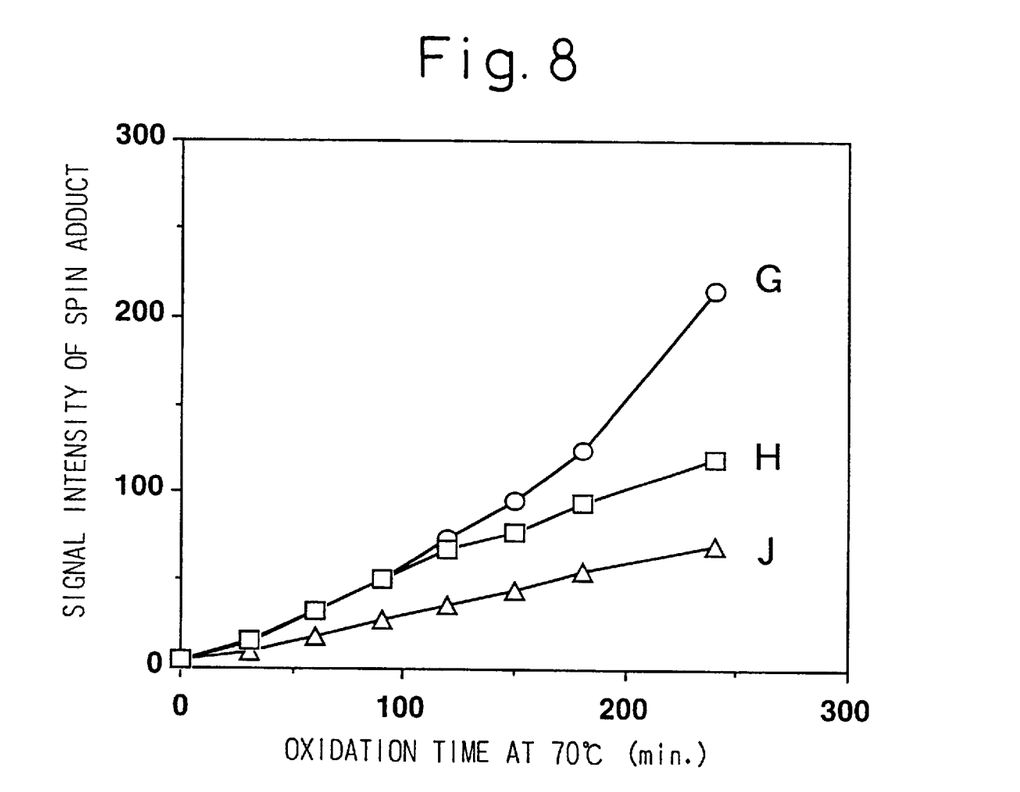
FIG. 8 is a graph expressing oxidation time at 70° C. on the horizontal axis following addition of hydrogen peroxide to a final concentration of 50 ppm, and the magnitude of spin adduct formed on the vertical axis (example of the active oxygen formation behavior of sake).

Measurement was performed under the same conditions and following the same procedure as Embodiment 1 with the exception of adding hydrogen peroxide to the samples and using a heating at 70° C. using the same three different types of commercially available finished sake G, H and J as Example 6. After taking out 5 g samples in the same manner as Example 1, adding hydrogen peroxide to a final concentration of 50 ppm, placing each sample in a 14.5 ml, stoppered, brown test tube, adding 0.1 ml of 2.55M PBN, and storing sealed while heating at 70° C., the active oxygen that formed was measured using an electron spin resonance apparatus. The graphs shown in FIG. 8 were respectively obtained for changes of the amount of spin adduct with passage of time, and values were obtained for active oxygen formation lag time and active oxygen formation activity (spin adduct signal intensity in the case of taking the predetermined time after the start of measurement to be 180 minutes). The results obtained in Example 6 were referred to for the sensory analysis.

The order of the magnitude of active oxygen formation activity of the three types of sake G, H and J was G>H>J, which was the same as the results after storage for 4 weeks at 40° C. of Example 6. Thus, differences were again observed between the three types of sake. In addition, according to the results of the sensory analysis, the degree of flavor deterioration was G>H>J (in order of strongest deterioration). It was therefore confirmed that the sake having the lowest active oxygen formation activity also had the lowest degree of flavor deterioration after storage and correspondingly the best flavor stability.

According to these results, similar results are obtained when sake is measured after 4 weeks of storage and when measurement is performed following addition of hydrogen peroxide. It was therefore confirmed that flavor stability can be predicted and evaluated by either of these methods, thus indicating that preliminary evaluation of flavor stability can be performed both rapidly and effectively for sake equally well by determining active oxygen formation lag time or by active oxygen formation activity.

Although the above has provided a detailed explanation of the present invention using its embodiments, the present invention is not limited to the above-mentioned examples, but rather can be suitably modified. Although oxidation reaction was measured for the samples at 60° C. or 70° C. in the embodiments, measurement is not limited to being performed at these temperatures, but rather can be suitably selected according to the thermal stability of the samples being measured and the ease of determination of active oxygen formation lag time. Since active oxygen formation lag times will become shorter if oxidation is measured at higher temperatures, it is possible to shorten measurement time. In order to facilitate easier measurement, similar evaluations can be performed by storing at room temperature and above, adding hydrogen peroxide to the samples, and so forth, to forcibly promote oxidation.

In the present invention, by investigating the formation behavior of active oxygen at the start of oxidative deterioration, which is thought to act as an initiator of oxidative deterioration in fermented alcoholic beverages such as beer, wine and sake, the oxidation resistance of the fermented alcoholic beverage can be evaluated, thus enabling preliminary evaluation of the flavor stability of that fermented alcoholic beverage both accurately and in a short time.

In addition, in the present invention, by investigating the formation behavior of active oxygen at the start of oxidative deterioration using an ESR apparatus at the stage of a semi-finished product in the production process, it is possible to accurately evaluate and predict the flavor stability of the fermented alcoholic beverage at the time it becomes a finished product.

We claim:

1. An analytical method for evaluating flavor stability of a fermented alcoholic beverage product using electron spin resonance comprising:

providing a fermented alcoholic beverage product together with a spin trapping agent in the presence of oxygen;

forming a spin adduct in the beverage product which comprises the spin trapping agent and active oxygen which is formed when the fermented alcoholic beverage product is placed in the presence of oxygen;

measuring an amount of spin adduct formed using an electron spin resonance apparatus;

determining a degree of oxidation resistance of the fermented alcoholic beverage product based upon the amount of spin adduct formed; and determining the flavor stability of the fermented alcoholic beverage product based upon the degree of oxidation resistance of the fermented alcoholic beverage product.

2. An analytical method for evaluating the flavor stability of the fermented alcoholic beverage product using electron spin resonance as set forth in claim 1 wherein the active oxygen is a hydroxyl radical.

3. An analytical method for evaluating the flavor stability of the fermented alcoholic beverage product using electron spin resonance as set forth in claim 1 wherein changes in the amount of spin adduct formed are measured successively at predetermined time intervals and are recorded to obtain a graph of the amount of spin adduct verses time and wherein an inflection point on said graph is identified and evaluated to determine the degree of oxidation resistance of the fermented alcoholic beverage product.

4. An analytical method for evaluating the flavor stability of the fermented alcoholic beverage product using electron spin resonance as set forth in claim 1 further comprising determining the amount of spin adduct at a predetermined time during said measurement step, and evaluating the degree of oxidation resistance of the fermented alcoholic beverage product based on said determined amount of spin adduct.

5. An analytical method for evaluating the flavor stability of the fermented alcoholic beverage product using electron spin resonance as set forth in claim 1 wherein the fermented alcoholic beverage is beer.

6. An analytical method for evaluating the flavor stability of the fermented alcoholic beverage product using electron spin resonance as set forth in claim 1 wherein the fermented alcoholic beverage is wine.

7. An analytical method for evaluating the flavor stability of the fermented alcoholic beverage product using electron spin resonance as set forth in claim 1 wherein the fermented alcoholic beverage is sake.

8. An analytical method for evaluating flavor stability of a fermented beverage product using electron spin resonance comprising:

providing a semi-finished fermented beverage product in a production process of the fermented alcoholic beverage product together with a spin trapping agent in the presence of oxygen;

forming a spin adduct in the semi-finished fermented beverage which comprises a spin trapping agent and active oxygen which is formed when the semi-finished fermented beverage product is placed in the presence of oxygen;

measuring an amount of spin adduct formed in the semi-finished fermented beverage product using an electron spin resonance apparatus;

determining a degree of oxidative resistance of the semi-finished fermented beverage product based upon the amount of spin adduct formed; and determining the flavor stability of the fermented alcoholic beverage product based upon the degree of oxidation resistance of the semi-finished fermented beverage product.

9. An analytical method for evaluating the flavor stability of the fermented alcoholic beverage product using electron spin resonance as set forth in claim 8 wherein the active oxygen is a hydroxyl radical.

10. An analytical method for evaluating the flavor stability of the fermented alcoholic beverage product using electron spin resonance as set forth in claim 8 wherein changes in the amount of spin adduct formed are measured successively at predetermined time intervals and are recorded to obtain a graph of the amount of spin adduct verses time and wherein an inflection point on said graph is identified and evaluated to determine the degree of oxidation resistance of the fermented alcoholic beverage product.

11. An analytical method for evaluating the flavor stability of the fermented alcoholic beverage product using electron spin resonance as set forth in claim 1.

12. An analytical method for evaluating the flavor stability of the fermented alcoholic beverage product using electron spin resonance as set forth in claim 8 wherein the semi-finished product comprises an alcoholic beverage product during or after a fermentation process.

13. An analytical method for evaluating the flavor stability of the fermented alcoholic beverage product using electron spin resonance as set forth in claim 8 wherein the fermented alcoholic beverage product is beer.

14. An analytical method for evaluating the flavor stability of the fermented alcoholic beverage product using electron spin resonance as set forth in claim 8 wherein the fermented alcoholic beverage product is wine.

15. An analytical method for evaluating the flavor stability of the fermented alcoholic beverage product using electron spin resonance as set forth in claim 8 wherein the fermented alcoholic beverage product is sake.

16. An analytical method for evaluating the flavor stability of the fermented alcoholic beverage product using electron spin resonance in claim 13 wherein the semi-finished product in the production process of beer is a semi-finished product as of completion of a wort boiling process.

17. An analytical method for evaluating the flavor stability of the fermented alcoholic beverage product using electron spin resonance in claim 14 wherein a semi-finished product in the production process of wine is a semi-finished product produced after treatment of fruit juice.

18. An analytical method for evaluating the flavor stability of the fermented alcoholic beverage product using electron spin resonance in claim 15 wherein a semi-finished product in the production process of sake is a semi-finished product as of completion of a sake mashing fermentation process.

* * * * *

UNITED STATES PATENT AND TRADEMARK OFFICE
CERTIFICATE OF CORRECTION

PATENT NO. : 5,811,305
DATED : September 22, 1998
INVENTOR(S) : Miyoko Ono et al.

It is certified that error appears in the above-identified patent and that said Letters Patent is hereby corrected as shown below:

Drawings,
Sheet 4, Figure 4, should read as follows:
-- --.

Signed and Sealed this

Thirteenth Day of June, 2006

JON W. DUDAS
*Director of the United States Patent and Trademark Office*